(12) United States Patent
Carlson et al.

(10) Patent No.: US 10,213,704 B2
(45) Date of Patent: Feb. 26, 2019

(54) METHODS AND SYSTEMS FOR REDUCING THE LEVEL OF ONE OR MORE IMPURITIES THAT ARE PRESENT IN A PRETREATED CELLULOSIC MATERIAL AND/OR DISTILLATE

(71) Applicant: POET Research Inc., Sioux Falls, SD (US)

(72) Inventors: David Charles Carlson, Emmetsburg, IA (US); Blake J. Gomer, Aberdeen, SD (US); Casey C. Jenks, Tripp, SD (US); Sharil Kirschman-Rollag, Beaver Creek, MN (US); Kristine Nicole Plack, Harrisburg, SD (US); Melissa R. Tille, Sioux Falls, SD (US)

(73) Assignee: Poet Research, Inc., Sioux Falls, SD (US)

( * ) Notice: Subject to any disclaimer, the term of this patent is extended or adjusted under 35 U.S.C. 154(b) by 393 days.

(21) Appl. No.: 14/993,285

(22) Filed: Jan. 12, 2016

(65) Prior Publication Data
US 2016/0121236 A1    May 5, 2016

Related U.S. Application Data

(62) Division of application No. 13/917,169, filed on Jun. 13, 2013, now Pat. No. 9,278,379.

(60) Provisional application No. 61/600,043, filed on Jun. 15, 2012.

(51) Int. Cl.
| | |
|---|---|
| *B01D 3/00* | (2006.01) |
| *C08B 1/00* | (2006.01) |
| *C12P 7/06* | (2006.01) |
| *C07C 29/88* | (2006.01) |
| *C12P 7/10* | (2006.01) |
| *C07C 29/80* | (2006.01) |
| *B08B 1/00* | (2006.01) |

(52) U.S. Cl.
CPC ............... *B01D 3/002* (2013.01); *B08B 1/00* (2013.01); *C07C 29/80* (2013.01); *C07C 29/88* (2013.01); *C08B 1/00* (2013.01); *C12P 7/06* (2013.01); *C12P 7/10* (2013.01); *C12P 2201/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 3,960,672 A | * | 6/1976 | Ester | ....................... C07C 29/84 |
| | | | | 203/18 |
| 3,990,952 A | * | 11/1976 | Katzen | .................... C07C 29/80 |
| | | | | 203/33 |
| 5,424,417 A | | 6/1995 | Torget et al. | |
| 6,022,419 A | | 2/2000 | Torget et al. | |
| 8,815,552 B2 | | 8/2014 | Narendranath et al. | |
| 2010/0233771 A1 | | 9/2010 | McDonald et al. | |
| 2012/0129234 A1 | | 5/2012 | McDonald et al. | |
| 2013/0065289 A1 | | 3/2013 | Carlson | |
| 2013/0143290 A1 | | 6/2013 | Narendranath | |
| 2013/0337521 A1 | | 12/2013 | Carlson et al. | |
| 2014/0024826 A1 | | 1/2014 | Narendranath et al. | |
| 2014/0209092 A1 | | 7/2014 | McDonald et al. | |
| 2014/0234911 A1 | | 8/2014 | Narendranath et al. | |

FOREIGN PATENT DOCUMENTS

| | | | | |
|---|---|---|---|---|
| WO | WO-03031560 A1 | * | 4/2003 | ............... C12C 5/00 |
| WO | WO 2011/159915 | | 12/2011 | |

OTHER PUBLICATIONS

Balat, Mustafa. "Production of bioethanol from lignocellulosic materials via the biochemical pathway: a review." Energy conversion and management 52.2 (2011): 858-875. (Year: 2011).*
U.S. Appl. No. 12/827,948, filed Jun. 30, 2010, Bootsma et al.
U.S. Appl. No. 13/209,170, filed Aug. 12, 2011, Bly.
U.S. Appl. No. 14/459,977, filed Aug. 14, 2014, Bootsma.
U.S. Appl. No. 14/465,177, filed Aug. 21, 2014, Narendranath et al.
U.S. Appl. No. 14/601,956, filed Jan. 21, 2015, Kwiatkowski.

* cited by examiner

*Primary Examiner* — Robert J Yamasaki
(74) *Attorney, Agent, or Firm* — Kagan Binder, PLLC

(57) ABSTRACT

The present invention relates to methods and systems for remediating one or more impurities (e.g., diacetyl) that are present in manufacturing an alcohol (e.g., ethanol) from cellulosic biomass. The methods and systems include reacting the one or more impurities with at least one treatment compound (e.g., an oxidizing agent, an alkali compound, or a mixture thereof) to form a reaction product that can be separated from the alcohol.

11 Claims, 13 Drawing Sheets

METHODS AND SYSTEMS FOR REDUCING THE LEVEL OF ONE OR MORE IMPURITIES THAT ARE PRESENT IN A PRETREATED CELLULOSIC MATERIAL AND/OR DISTILLATE

RELATED APPLICATION

This application is a divisional Patent Application of nonprovisional patent application Ser. No. 13/917,169, filed Jun. 13, 2013, which claims priority to U.S. Provisional Application Ser. No. 61/660,043, filed Jun. 15, 2012, which applications are incorporated herein by reference in their entireties.

FIELD OF THE INVENTION

The present invention relates methods and systems for remediating one or more impurities (e.g., diacetyl) that are present in manufacturing an alcohol (e.g., ethanol) from cellulosic biomass. The methods and systems include reacting the one or more impurities with at least one treatment compound (e.g., an oxidizing agent, an alkali compound, or a mixture thereof) to form a reaction product that can be separated from the alcohol.

BACKGROUND

Alcohol (e.g., ethanol and/or butanol) and other fermentation products may be produced from grain-based feedstocks (e.g. corn, sorghum/milo, barley, wheat, soybeans, etc.), from sugar (e.g. from sugar cane, sugar beets, etc.), and from biomass (e.g. from cellulosic feedstocks such as switchgrass, corn cobs and stover, wood or other plant material).

In a biorefinery configured to produce ethanol from biomass such as cellulosic feedstocks as indicated above, ethanol can be produced from lignocellulosic material (e.g. cellulose and/or hemi-cellulose). The biomass is typically prepared so that sugars in the cellulosic material (such as glucose from the cellulose and xylose from the hemi-cellulose) can be accessed and fermented into a fermentation product that includes ethanol (among other things). The fermentation product can then be transferred to a distillation system, where the ethanol can be recovered by distillation and dehydration. Other bioproducts such as lignin and organic acids may also be recovered as co-products.

In addition to generating ethanol (or other desired fermentation product) a number of ancillary chemicals may also be produced during one or more of biomass pretreatment, saccharification, fermentation, or even distillation. Such chemicals include substances such as acetic acid, furfural (furan-2-carbaldehyde), and diacetyl (2,3-butanedione). Some of these compounds may be recovered or recycled, but other compounds require management or remediation in order for the cellulosic biorefinery to operate effectively. In particular, the presence of diacetyl may be particularly problematic as it concentrates along with ethanol during distillation and molecular sieving. Not only can diacetyl cause green coloring of the ethanol to an undue degree (thereby limiting the ethanol's downstream uses), diacetyl can also cause the ethanol to become more acidic over time. For fuel ethanol these are typically undesirable traits and can make remediation of the diacetyl desirable.

One common technique for managing undue amounts of diacetyl in cellulosic ethanol includes aging the ethanol so that the diacetyl breaks down naturally. Another common technique includes blending the ethanol/diacetyl mixture with a much larger volume of starch derived ethanol so as to dilute the diacetyl, thereby decreasing the concentration of diacetyl.

Unfortunately, as cellulosic ethanol becomes more prevalent, the volumes can reach levels such that storage for long periods to "age" the diacetyl can be uneconomical, and blending may become difficult due to the vast amounts of starch based ethanol required.

It would be advantageous to provide for systems and methods for cellulosic fermentation product treatment that can rapidly and economically remediate diacetyl. It would further be advantageous to provide for systems and methods for such treatment that integrates into the functionality of a commercial scale ethanol production facility.

SUMMARY OF THE INVENTION

The present invention relates to systems and methods for treating cellulosic fermentation products and/or related distillate compositions in order to reduce one or more undesirable compounds such as diacetyl to a desirable level. The present invention involves contacting a composition that includes ethanol and diacetyl (e.g., a distillate, fermentation product, and the like) with at least one treatment compound so that the at least one treatment compound reacts with the diacetyl to form a reaction product thereby reducing the concentration of the diacetyl. Preferably, at least a portion of the reaction product can then be separated from the ethanol.

Advantageously, systems and methods according to the present invention can reduce the concentration of, e.g., diacetyl to a level so that diacetyl does not impact the color and/or pH of the final ethanol product to an undue degree. In addition, systems and methods according to the present invention can reduce the concentration of diacetyl in ethanol in a cost effective and rapid manner.

According to one aspect of the present invention, a method of reducing the concentration of diacetyl that is present in a pretreated cellulosic material includes: providing a pretreated cellulosic material that includes at least one monosaccharide and diacetyl; and contacting the pretreated cellulosic material with at least one treatment compound so that the at least one treatment compound reacts with the diacetyl to form a reaction product thereby reducing the concentration of the diacetyl. The at least one treatment compound is chosen from an oxidizing agent, an alkali compound, and mixtures thereof.

According to another aspect of the present invention, a method of reducing the concentration of diacetyl that is present in a distillate includes providing a pretreated cellulosic material; subjecting the pretreated cellulosic material to a fermentation process to form a fermentation product that includes an alcohol and diacetyl; distilling the fermentation product to form a distillate that includes the alcohol and the diacetyl; and contacting the distillate with at least one treatment compound so that the at least one treatment compound reacts with the diacetyl to form a reaction product thereby reducing the concentration of the diacetyl and forming a treated distillate, wherein the at least one treatment compound is chosen from an oxidizing agent, an alkali compound, and mixtures thereof.

According to another aspect of the present invention, a system for reducing the concentration of diacetyl that is present in a pretreated cellulosic material includes: a source of a fermentation product that includes an alcohol and diacetyl; a distillation system in fluid communication with the source of a fermentation product; a source of at least one treatment compound; and a treatment system in fluid communication with the distillation system and the source of at least one treatment compound. The at least one treatment compound is chosen from an oxidizing agent, an alkali compound, and mixtures thereof. The distillation system can distill the fermentation product to form a distillate that includes the alcohol and the diacetyl. The treatment system causes the least one treatment compound to contact the distillate so that the at least one treatment compound reacts with the diacetyl to form a reaction product thereby reducing the concentration of the diacetyl and forming a treated distillate.

In preferred embodiments, the treatment compound includes sodium hydroxide, hydrogen peroxide and mixtures thereof.

DETAILED DESCRIPTION

Figure 1A:
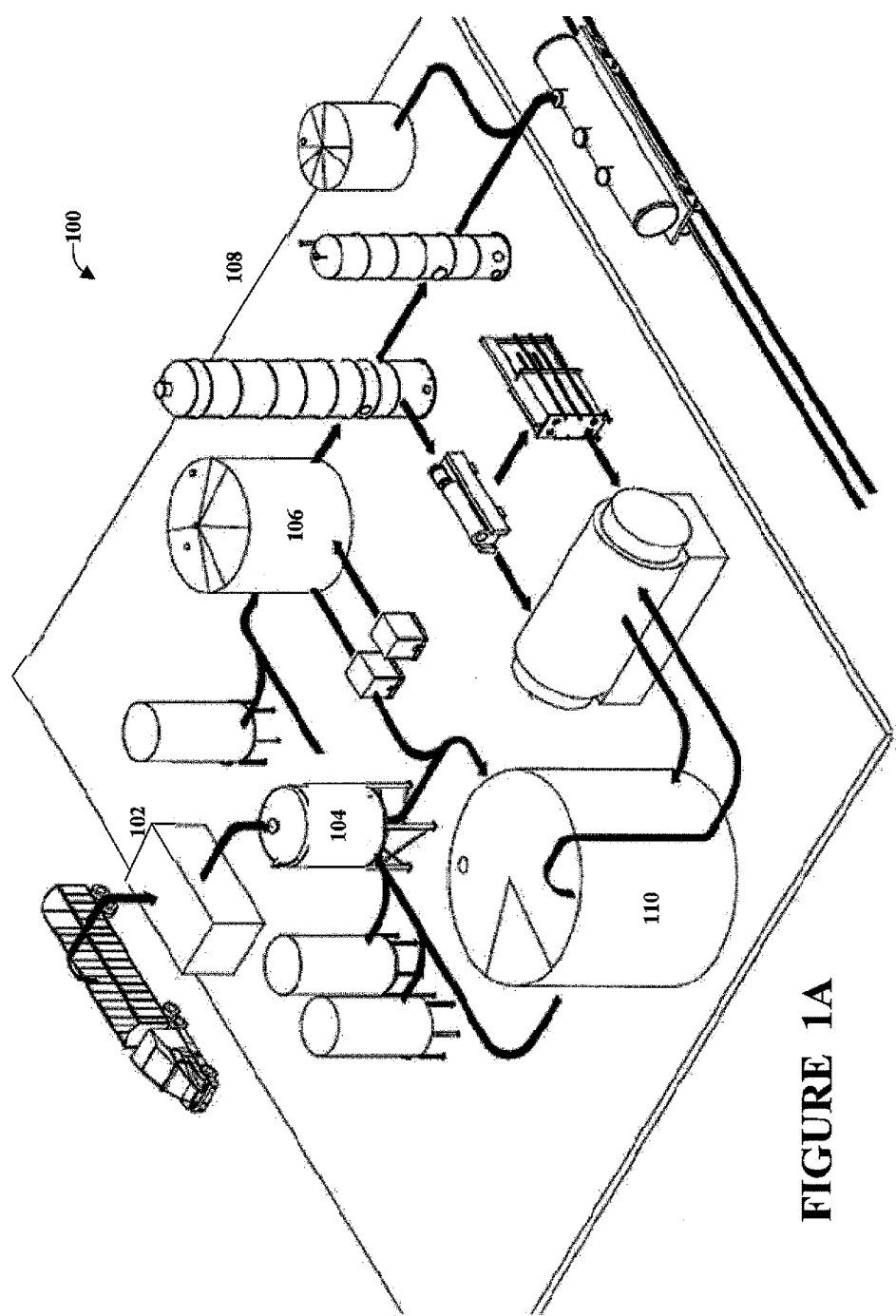
FIG. 1A is a perspective view of a biorefinery comprising an ethanol production facility, in accordance with some embodiments.

The present invention will now be further described with reference to exemplary embodiments. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to facilitate explaining the present invention. The features and advantages of embodiments may be better understood with reference to the drawings and discussions that follow.

The present invention relates to systems and methods to reduce the concentration of one or more undesirable components that are generated during at least one of pretreating, saccharification, or fermentation of cellulosic biomass material, or distillation of fermented cellulosic biomass material.

Cellulosic biomass material is well-known and includes polysaccharides such as cellulose and/or hemicellulose. Exemplary cellulosic feedstock for use in the present invention includes one or more of wood material, switch grass, agricultural waste, municipal waste, bagasse, etc. In some embodiments, a preferred cellulosic biomass material includes material from the corn plant, such as corn cobs, corn plant husks and corn plant leaves and corn stalks (e.g. at least upper half or three-quarters portion of the stalk) (also referred to as corn stover). For example, the corn plant material may include any of (by weight) up to 100 percent cobs, up to 100 percent husks/leaves, approximately 50 percent cobs and approximately 50 percent husks/leaves, approximately 30 percent cobs and approximately 50 percent husks/leaves and approximately 20 percent stalks, or any of a wide variety of other combinations of cobs, husks/leaves and stalks from the corn plant. According to some embodiments, the lignocellulosic plant material of the biomass (from the corn plant) can include (by weight) cellulose at about 30 to 55 percent, hemicellulose at about 20 to 50 percent, and lignin at about 10 to 25 percent. According to alternative embodiments, the lignocellulosic plant material may include fiber from the corn kernel (e.g. in some combination with other plant material). According to one preferred embodiment, the biomass may include at least 20 to 30 percent corn cobs (by weight) with corn stover and other matter.

The cellulosic biomass material is preferably selected to convert one or more polysaccharides such as hemicellulose or cellulose into one or more monosaccharides such as pentose (e.g., xylose) or hexose (e.g., glucose), which can be used to generate one or more fermentation products. Exemplary fermentation products include alcohol (e.g., ethanol, butanol, and the like) due to the utility of alcohol as a fuel. However, any fermentation product resulting from the conversion of cellulosic materials into sugars and biological conversion is considered within the scope of this disclosure.

Biorefinery plant facilities for producing alcohol from biomass are well known. Briefly, exemplary biorefinery plant facilities are described herein in connection with FIGS. 1A and 1B. FIG. 1A shows biorefinery 100 that includes an ethanol production facility configured to produce ethanol from biomass. The exemplary biorefinery 100 includes an area 102 where biomass is delivered and prepared to be supplied to the ethanol production facility. The cellulosic ethanol production facility 100 includes equipment for preparation 102, pre-treatment 104 and conversion of the biomass into material (e.g., sugars) suitable for fermentation into one or more fermentation products in a fermentation system 106. The cellulosic ethanol production facility 100 includes a distillation system 108 in which the fermentation product is distilled and dehydrated into ethanol. As shown in FIG. 1A, a waste treatment system 110 includes an anaerobic digester and a generator. Waste treatment system 110 can include additional equipment configured to treat, process, and recover components from the cellulosic ethanol production process, such as a solid/waste fuel boiler, anaerobic digester, or other biochemical or chemical reactors.

Figure 1B:
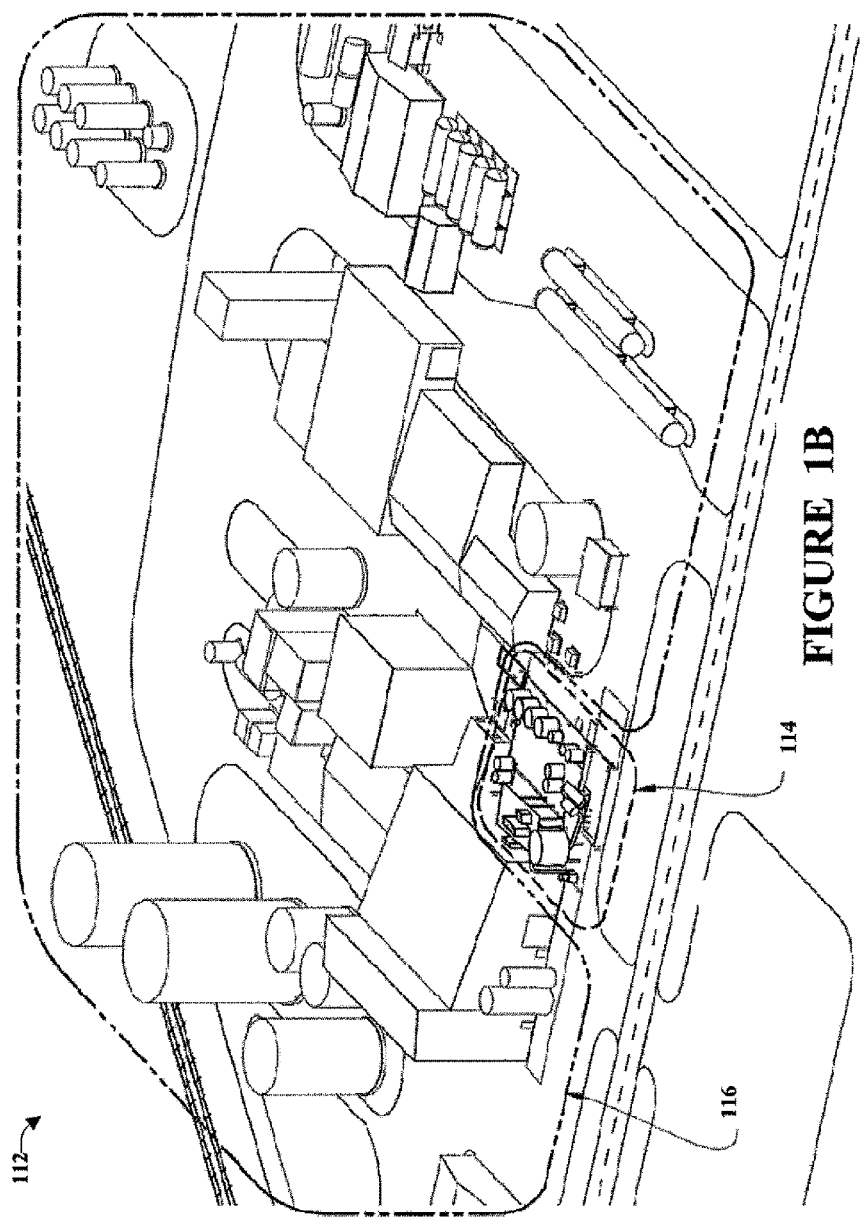
FIG. 1B is another perspective view of a biorefinery comprising an ethanol production facility, in accordance with some embodiments.

FIG. 1B illustrates that a biorefinery 112 may include a cellulosic ethanol production facility 114 (which produces ethanol from lignocellulosic material and components of the corn plant) co-located with a corn-based ethanol production facility 116 (which produces ethanol from starch contained in the endosperm component of the corn kernel). As indicated in FIG. 1B, by co-locating the two ethanol production facilities, certain plant systems may be shared, for example, systems for dehydration, storage, denaturing and transportation of ethanol, energy/fuel-to-energy generation systems, plant management and control systems, and other systems. Corn fiber (a component of the corn kernel), which can be made available when the corn kernel is prepared for milling (e.g. by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g. a cellulosic ethanol production facility) may be co-located with other types of plants and facilities, for example an electric power plant, a waste treatment facility, a lumber mill, a paper plant, or a facility that processes agricultural products.

Figure 2:
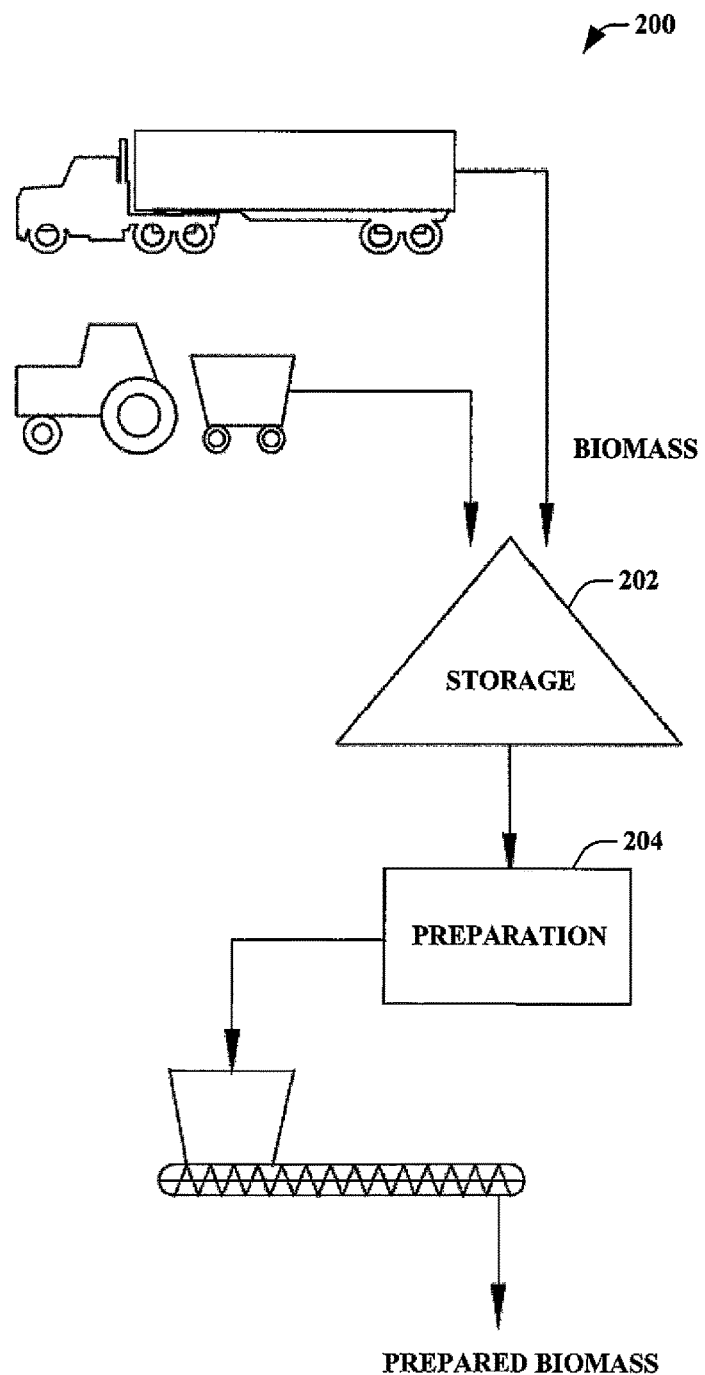
FIG. 2 is a process flow diagram illustrating the preparation of biomass, in accordance with some embodiments.

FIG. 2 illustrates an exemplary system 200 for preparation of biomass delivered to a biorefinery 100. The biomass preparation system 200 may include equipment for receiving/unloading the biomass, cleaning (e.g. removal of foreign matter), grinding (e.g. milling, reduction or densification), and transport and conveyance for processing at the plant. According to an exemplary embodiment, biomass in the form of corn cobs and stover may be delivered to the biorefinery and stored 202 (e.g. in bales, piles or bins, etc.) and managed for use at the facility. As shown, system 200 also includes preparation system 204, which is configured to prepare any of a wide variety of types of biomass (e.g. plant material) for treatment and processing into ethanol and other bioproducts at the plant.

Figure 3A:
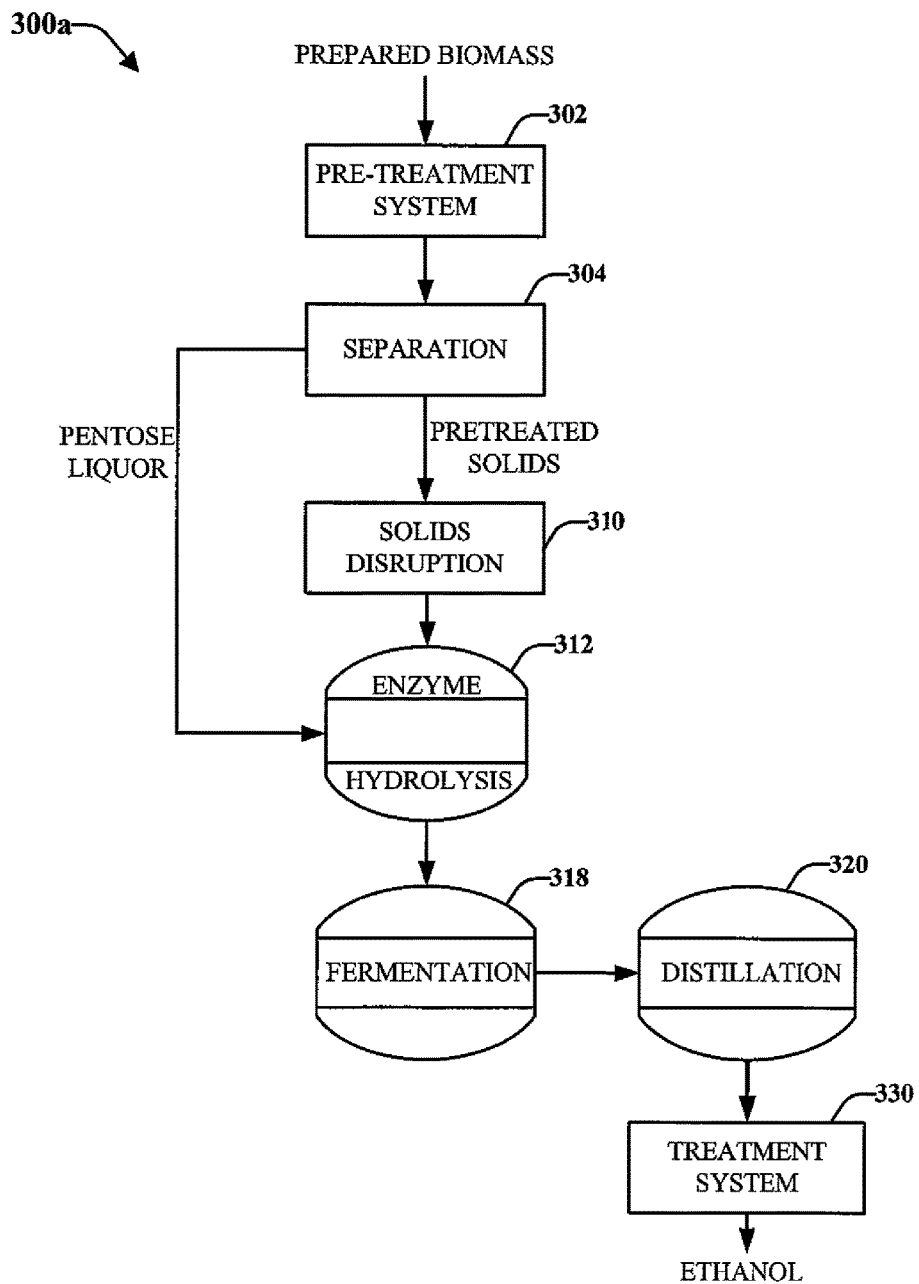
FIGS. 3A to 3C are process flow diagrams illustrating examples of ethanol production processes from biomass to ethanol, in accordance with some embodiments.
Figure 3B:
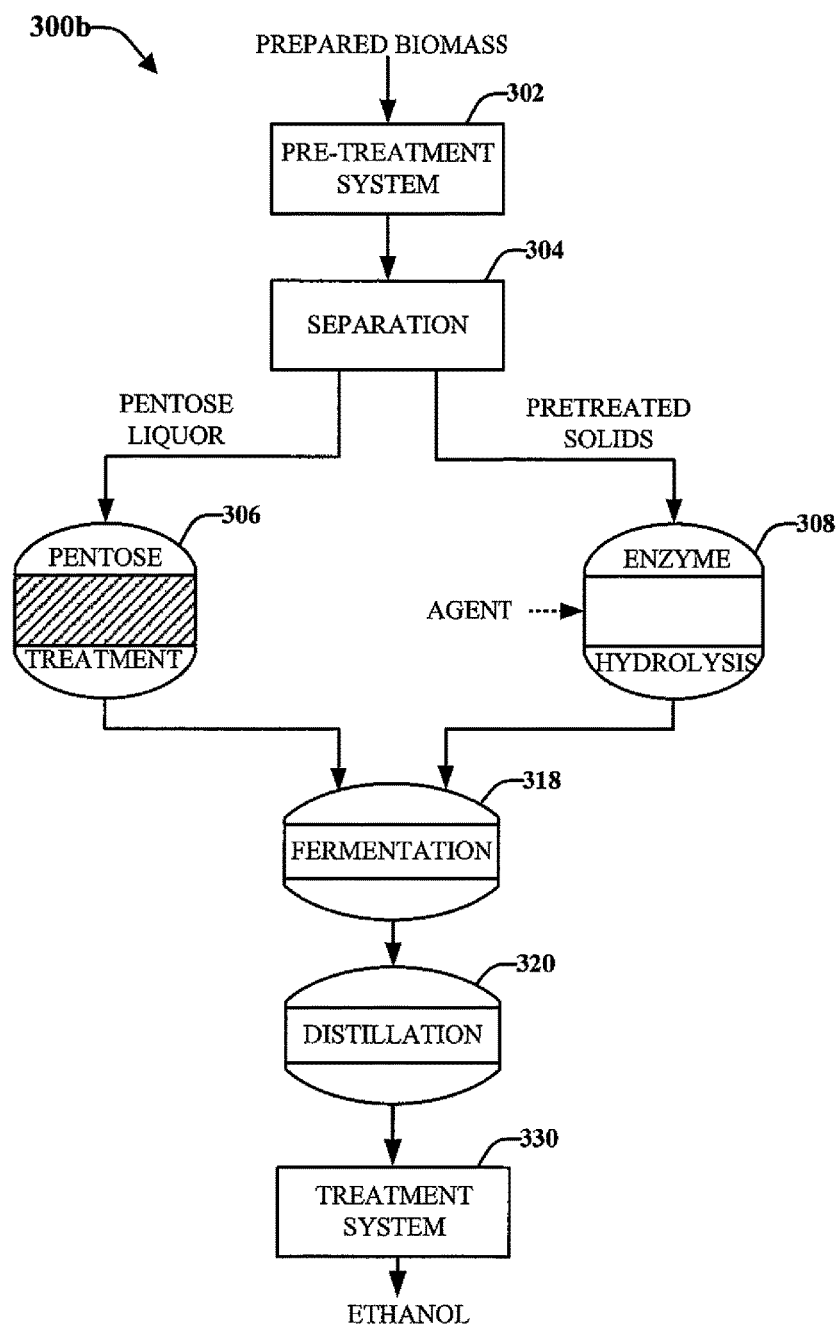
Figure 3C:
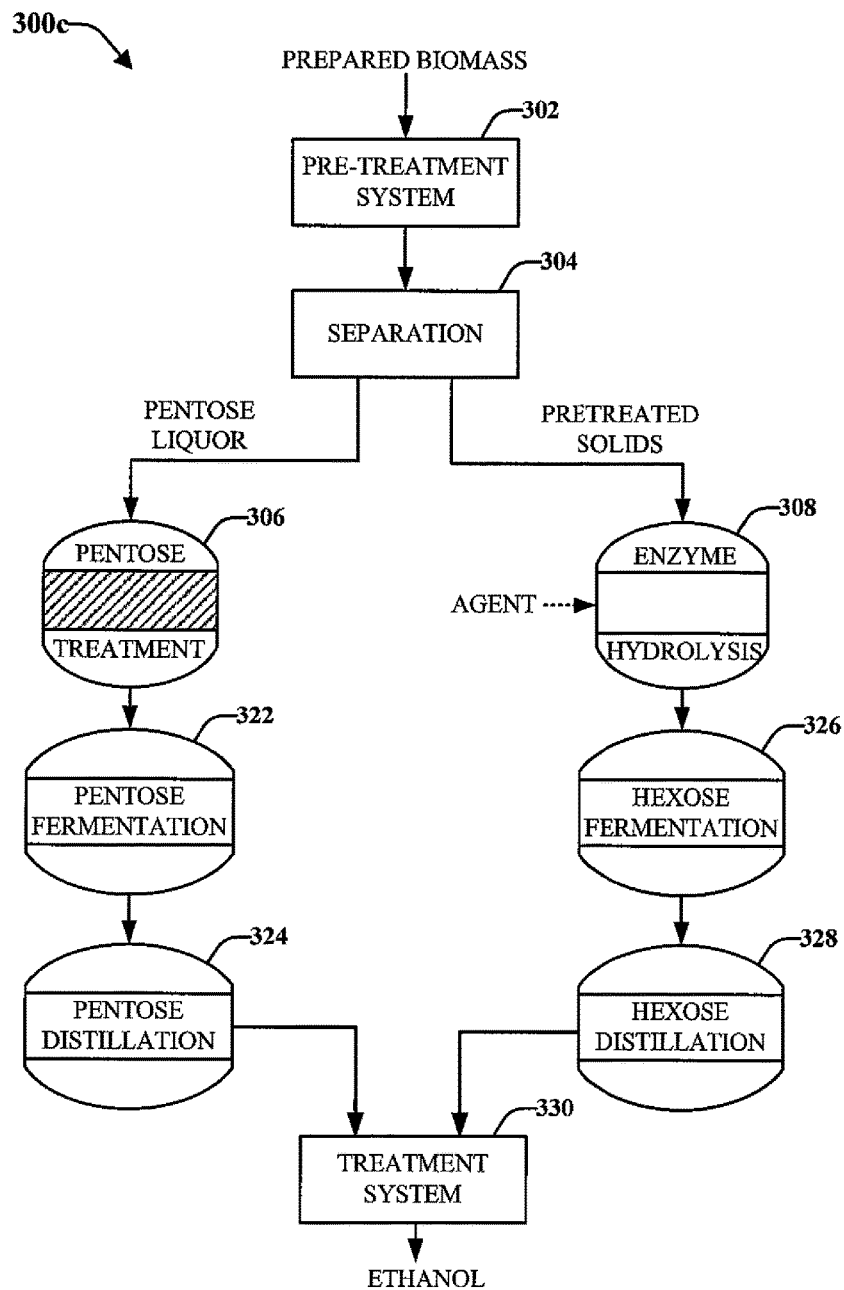

FIGS. 3A to 3C illustrate exemplary process flow diagrams 300a, 300b and 300c for processing biomass that has been prepared, e.g., as described above with respect to FIG. 2. The process flow diagrams shown in FIGS. 3A to 3C illustrate pretreating, fermenting, distillation, and treatment of the distillate from distillation. An example of a treatment system for treating distillate to reduce the concentration of diacetyl according to the present invention is described in more detail below in connection with FIG. 4.

As shown in FIGS. 3A to 3C, after preparing the biomass, e.g., in system 200, the biomass is mixed with water into a slurry and is pre-treated via a pre-treatment system 302. In the pre-treatment system 302, the biomass can be at least partially broken down (e.g. by hydrolysis) into one ore more oligosaccharides and/or monosaccharides (e.g., pentoses (C5 sugars) and/or hexoses (C6 sugars)). Exemplary monosaccharides include xylose and glucose. Pretreatment may include the addition of one more chemicals (e.g., an acid) to promote hydrolysis of hemicelluose and/or cellulose in the biomass so as to generate one or more oligosaccharides and/or monosaccharides. Such pretreatment of cellulosic biomass is well-known and is disclosed in, e.g., U.S. Pat. No. 5,424,417 (Torget et al.) and U.S. Pat. No. 6,022,419 (Torget et al.), wherein the entireties of said documents are incorporated herein by reference for all purposes.

After pretreatment 302, as shown in FIGS. 3A-3C, separation system 304 can separate a liquid fraction (e.g. a stream including C5 sugars, known as pentose liquor) and a solids fraction (e.g. a stream including cellulose from which the C6 sugars can be made available via solids disruption and/or enzymatic hydrolysis (discussed below)).

As shown in FIG. 3A, the solids in the solid stream from separation system 304 are disrupted via a disruption system 310 to make the solids more accessible to enzymes during enzymatic hydrolysis of the solids to generate one or more C6 sugars from cellulose. Techniques for disrupting biomass solids to increase accessibility during enzymatic hydrolysis are well-known and include mechanical disruption, sonic disruption, and/or steam explosion.

The C5-sugar-containing liquid component (C5 stream or pentose liquor) from separation system 304 may be returned to a joint enzyme hydrolysis system 312 which may enzymatically generate sugars from a combined solids and liquids stream. Subsequently, the slurry from system 312 may enter a fermentation system 318 so that at least one of an oligosaccharide and/or a monosaccharide in the pretreated cellulosic material can be fermented to generate a fermentation product that includes an alcohol and diacetyl.

After fermentation in system 318, the fermentation product can be distilled in distillation system 320 to form a distillate that includes an alcohol (e.g., ethanol) and diacetyl. The distillate may also include lignin stillage.

As shown in FIG. 3A, the ethanol from distillation system 320 can be processed by a treatment system 330 according to the present invention for remediation of one or more undesired components (e.g., reduce the concentration of diacetyl in the ethanol).

After separation system 304 in each of FIGS. 3B and 3C, the C5-sugar-containing liquid component (C5 stream or pentose liquor) may be treated in a pentose cleanup treatment system 306. During treatment of the C5 and/or C6 stream, components may be processed to recovered byproducts, such as organic acids and lignin. The C6-sugar-containing pretreated solids component may be treated in a solids treatment system 308 using enzyme hydrolysis to generate sugars. In some embodiments, the solids component may be treated in an effort to remove lignin and other non-fermentable components in the C6 stream (or to remove components such as residual acid or acids that may be inhibitory to efficient fermentation) in addition to hydrolyzing (such as enzyme hydrolysis) the solids component to access the C6 sugars in the cellulose.

Optionally, enzyme hydrolysis efficiency may be increased through the addition of an agent. Such agents may include anaerobic membrane digester effluent, clarified thin stillage, wet cake, whole stillage, other viable protein source, or combinations thereof.

Optionally, the hexose sugars generated at enzyme hydrolysis system 308 may also be treated in a manner similar to pentose treatment system 306 via a hexose treatment system (not shown). The removed components during treatment and production of ethanol from the biomass from either or both the C5 stream and the C6 stream (or at distillation) can be treated or processed into bioproducts or into fuel (such as lignin for a solid fuel boiler or methane produced by treatment of residual/removed matter such as acids and lignin in an anaerobic digester) or recovered for use or reuse.

In accordance with the embodiment shown in FIG. 3B, the resulting treated pentose liquor from treatment system 306 and the hexose sugar from enzyme hydrolysis system 308 can be combined for co-fermentation in a fermentation system 318 to generate a fermentation that includes an alcohol (e.g., ethanol) and optionally one or more impurities such as diacetyl. Typically, a fermenting organism (ethanologen) is used in the fermentation system 318. The selection of an ethanologen may be based on various considerations, such as the predominant types of sugars supplied to fermentation system 318.

As shown in FIG. 3B, the fermentation product from the fermentation system 318 is supplied to a distillation system 320 where the alcohol such as ethanol is recovered. Dehydration and/or denaturing of the ethanol produced from the C5 stream and the C6 stream may be performed either separately or in combination. As described with respect to FIG. 3A, the ethanol from distillation system 320 can be processed by a treatment system 330 according to the present invention for the remediation of one or more undesired components (e.g., diacetyl).

Also, any stillage from the distillation system 320 may then be treated at a lignin separation system (not shown) to generate a liquid component and a solid wet cake. The wet cake may then be supplied to an Anaerobic Membrane Bioreactor (AnMBR) for further treatment, in some embodiments.

In accordance with the embodiment shown in FIG. 3C, the treated pentose liquor from treatment system 306 may be fermented in a pentose fermentation system 322, and the fermentation product from fermentation system 322 may be supplied to a pentose distillation system 324 for ethanol recovery. Likewise, the pretreated solids from separation system 304 may be supplied to enzyme hydrolysis system 308 to generate hexose sugars. The hexose sugars can be provided to a hexose fermentation system 326 to generate a fermentation product. The fermentation product from system 326 can be supplied to a hexose distillation system 328 for ethanol recovery.

The ethanol from the pentose distillation system 324 and the hexose distillation system 328 can be processed by a treatment system 330 according to the present invention for the remediation of one or more undesired components (e.g., diacetyl).

Also, any stillage from the distillation system 324 and/or distillation system 328 may then be treated at a lignin separation system (not shown) to generate a liquid component and a solid wet cake. The wet cake may then be supplied to an Anaerobic Membrane Bioreactor (AnMBR) for further treatment, in some embodiments.

The present invention relates to systems and methods to reduce the concentration of one or more undesirable components (also referred to herein as "remediation" of one or more undesirable components) that are generated during at least one of pretreating, saccharification, or fermentation of cellulosic biomass material, or distillation of fermented cellulosic biomass material.

In some embodiments, the undesired component includes diacetyl (2,3-butanedione). This is due at least in part to the impact that diacetyl can have on the color and/or pH of the quality of the final ethanol fuel product generated in a cellulosic ethanol plant. It is considered within the scope of this disclosure that additional undesirable components may also be remediated through the systems and methods disclosed herein. As such, no undue limitations should be placed upon components being remediated.

Accordingly, in some embodiments, a method according to the present invention includes reducing the concentration of diacetyl that is present in a pretreated cellulosic material and/or distillate by contacting the pretreated cellulosic material and/or distillate with at least one treatment compound so that the at least one treatment compound reacts with the diacetyl to form a reaction product thereby reducing the concentration of the diacetyl.

The reaction of the diacetyl with the treatment compound can convert the diacetyl (boiling point 88° C.) into a relatively less volatile reaction product such that a mixture of the ethanol and the reaction product can be subjected to a separation process that takes advantage of the lower boiling point of the reaction product thereby facilitating the purification of the ethanol with respect to the impurity diacetyl (or the reaction product thereof).

One or more treatment compounds can be selected so as to react with an impurity such as diacetyl and form a reaction product so as to reduce the concentration of the diacetyl. Preferably, the one or more treatment compounds are selected so that the reaction product is readily separated from the pretreated cellulosic material and/or distillate (and ultimately the alcohol such as ethanol). In some embodiments, the treatment compounds includes an oxidizing agent, an alkali compound, and mixtures thereof. In some embodiments, the oxidizing agent includes hydrogen peroxide. In some embodiments, the alkali compound includes sodium hydroxide.

In some embodiments, the concentration of diacetyl is reduced so that the color and/or pH are within one or more specifications for selling ethanol as a fuel. For example, preferably the diacetyl concentration is decreased so that the treated ethanol product from distillation is within product color specifications for selling ethanol as a fuel (i.e., is not green in color to an undue degree). Diacetyl can cause ethanol to be green to an undue degree at even 20-30 ppm in some instances. In some embodiments according to the present invention, the color of the ethanol after remediation according to the present invention is clear and bright. Typically, the ethanol is separated from the reaction product via, e.g., a re-vaporization process before the ethanol comes within final color specifications. For example, when sodium hydroxide is added to a ethanol/diacetyl mixture the color changes from a yellow-green (color of ethanol/diacetyl mixture) to a dark yellow-orange due to the reaction between sodium hydroxide and diacetyl.

With respect to pH, diacetyl can cause ethanol to be out of specification for sale as fuel because diacetyl can degrade into acid. The stoichiometric degradation of 1.0 ppm diacetyl yields 1.4 ppm acetic acid. Remediation of diacetyl according to the present invention preferably causes an increase in pH of the ethanol product to be sold as fuel so that the ethanol product is within one or more specifications for the sale of the ethanol product as fuel. For example, preferably the pretreated cellulosic material and/or distillate is contacted with an amount of an alkali compound (e.g., sodium hydroxide) so that the pH of the pretreated cellulosic material and/or distillate is at least 10, even more preferably at least 12.

In terms of the concentration level of diacetyl, the concentration of diacetyl in the final ethanol product (e.g., after re-vaporization discussed below) is preferably in an amount of 100 parts per million or less, 50 parts per million or less, 20 parts per million or less, or preferably even 10 parts per million or less.

At least one advantage of the remediation techniques of the present invention is the relative decrease in time period required to remediate a given amount of diacetyl as compared to "aging" a mixture for the diacetyl to break down. In some embodiments, wherein the concentration of diacetyl in the distillate can be reduced from at least 50, at least 100, or even at least 200 parts per million to 40, 20, 10, or even 5 parts per million or less in a time period of 60, 30, 20, or even 10 minutes or less.

Optionally, a method of remediation according to the present invention can include exposing pretreated cellulosic material and/or distillate to ultraviolet radiation to degrade one or more impurities and thereby reduce the concentration thereof of such impurities. The material to be remediated can be exposed to ultraviolet light at any time such as before, during, and/or after contacting the material with at least one treatment compound as described herein.

After the at least one treatment compound reacts with the diacetyl to form a reaction product, at least a portion of the reaction product and/or at least a portion of any residual diacetyl can be separated from the ethanol so as to increase the concentration of the ethanol. Preferably, after separating at least a portion of the reaction product and/or at least a portion of any residual diacetyl from the ethanol, the ethanol satisfies one or more specifications with respect to at least diacetyl and/or pH for selling ethanol as fuel.

The reaction product and/or any residual diacetyl can be separated from the alcohol by any technique. An exemplary separation technique includes vaporizing (also referred to as "re-vaporizing" in the context of occurring after distillation of a fermentation product) a mixture (e.g., a distillate) including at least alcohol, the reaction product of diacetyl and at least one treatment compound, and any residual diacetyl. Vaporizing is preferably performed under conditions to form a liquid fraction and a vapor fraction, where the vapor fraction includes at least a portion of the alcohol and the concentration of the alcohol in the vapor fraction is higher as compared to the concentration of the alcohol in the initial mixture (e.g., the distillate). In some embodiments, the vapor fraction from the vaporization process includes at least 100 proof ethanol, preferably at least 120 proof ethanol, and even preferably at least 150 proof ethanol.

Also, the liquid fraction from the vaporization process preferably includes at least a portion of the reaction product and the concentration of the reaction product in the liquid fraction is higher as compared to the concentration of the reaction product in the initial mixture (e.g., the distillate).

Figure 4:
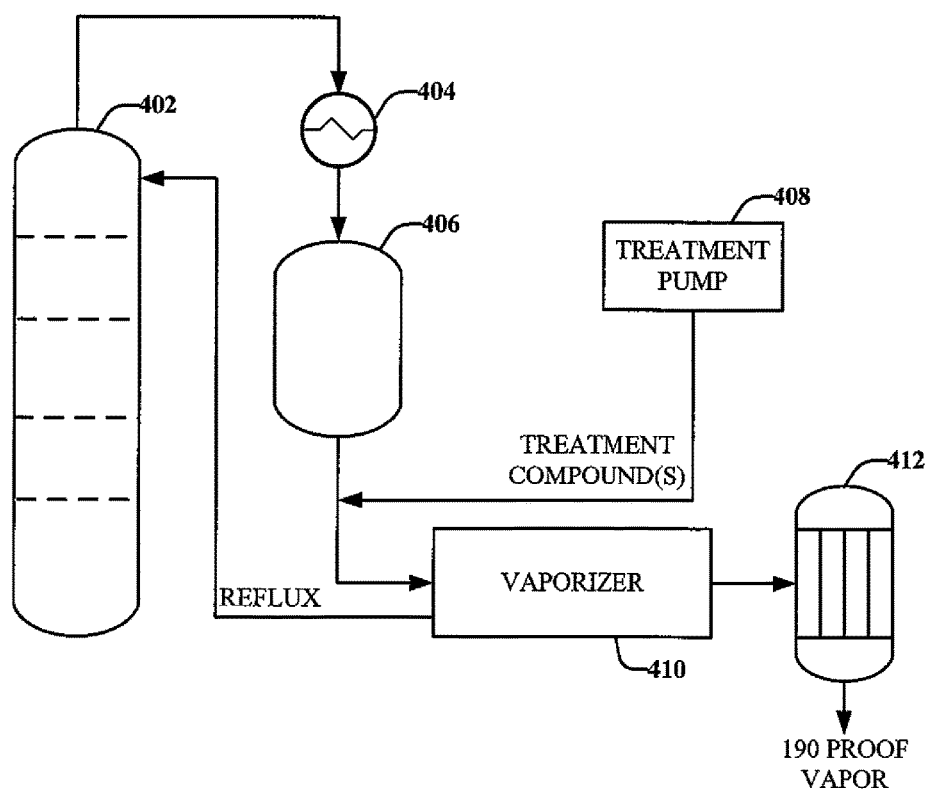
FIG. 4 is a process flow diagram illustrating the remediation treatment process, in accordance with some embodiments.

FIG. 4 illustrates an exemplary system for reducing the concentration of diacetyl that is present in a pretreated cellulosic material. The individual equipment/components described in connection with FIG. 4 are well-known and commercially available. As shown, a rectifier 402 is illustrated that delivers a mixture 190 proof ethanol vapor and relatively high levels of the diacetyl to condenser 404 where the mixture is condensed. The resulting condensed ethanol solution is collected in a rundown tank 406. Optionally, a portion of the ethanol collected in the rundown tank can be returned to the rectifier 402 as a reflux (not shown). The remaining ethanol/diacetyl solution is mixed with a treatment compound prior to being supplied to a vaporizer 410. A treatment pump 408 drives the treatment compound and ensures accurate dosing. In the vaporizer 410 the mixed liquid is heated. The resulting vapor is supplied to a superheater 412 which results in a 190 proof ethanol vapor stream that has virtually all the undesirable compounds (e.g., diacetyl) removed. A purge stream from the vaporizer 410 is supplied back to the rectifier 402.

EXAMPLES

Example 1

The first example proceeded using a 7% $H_2O_2$ solution that was used for diacetyl mitigation during a batch distillation run. A known volume of cellulosic ethanol was heated to 60° C. then treated with 10% by volume of a 7% $H_2O_2$ solution. The ethanol was kept at 60° C. with constant stirring after the treatment and samples were taken for HPLC analysis following the treatment at 0 hour, 1 hour and 2 hour; then the sample was distilled. The results show a 63% reduction in diacetyl immediately following the treatment with a 91% reduction at one hour post treatment. The HPLC results are shown below in Table 1.

TABLE 1

| $H_2O_2$ Mitigation - 10% $H_2O_2$ (7% $H_2O_2$) | Acetic Acid ppm | Ethanol % v/v | Diacetyl ppm | Color | Reduction of Diacetyl % |
|---|---|---|---|---|---|
| 100 proof | 27 | 56 | 123 | slight green | |
| Mitigation-0 hr @60 C. | 299 | 53 | 45 | clear | 64 |
| Mitigation-1 hr @60 C. | 203 | 53 | 12 | clear | 91 |
| Mitigation-2 hr @60 C. | 168 | 53 | ND | clear | 100 |
| Distillate | ND | 100 | ND | clear | 100 |
| Still Bottoms | 181 | 47 | ND | clear | 100 |

Example 2

The second example proceeded using a 1.0N solution of sodium hydroxide (NaOH). A known volume of cellulosic ethanol was heated to 60° C., treated with 0.2% by volume of a 1.0N NaOH solution, and then distilled. Duplicate test results are shown in Table 2 below. The distillate and the still bottoms are within industry specifications.

TABLE 2

| NaOH Mitigation-0.2% NaOh (1.0N) Sample Description | Acetic Acid ppm | Ethanol % v/v | Diacetyl ppm | Color | pH | pHe |
|---|---|---|---|---|---|---|
| Feed-100 proof | 34 | 50 | 102 | slight green | 4.3 | |
| 0.2% NaOH (1.0N) | 60 | 50 | ND | clear | 11.4 | |
| Distillate | ND | 101 | 33 | clear | | 7.3 |
| Still Bottoms | 107 | 29 | ND | orange-brown | 7.5 | |
| Feed-100 proof | 25 | 52 | 100 | slight green | 4.4 | |
| 0.2% NaOH (1.0N) | 53 | 52 | ND | clear | 11.5 | |
| Distillate | ND | 95 | 33 | clear | | 8.3 |
| Still Bottoms | 119 | 30 | ND | orange-brown | 8.1 | |

Example 3

A mitigation strategy to treat the cellulosic ethanol with a combination of $H_2O_2$ and NaOH was devised. Based on previous results for hydrogen peroxide and sodium hydroxide mitigation, several tests were conducted to determine the optimum dosage of both. Table 3 shows the results for a mitigation treatment of 1% by volume of a 7% $H_2O_2$ solution followed by 0.01% by volume of a 50% w/w NaOH solution. The results show that diacetyl is converted to acetic acid and the distillate color is clear.

TABLE 3

H$_2$O$_2$ + NaOH Mitigation-
1% H$_2$O$_2$ (7%) + 0.01%
NaOH (50%)

| Sample Description | Mass (g) | Acetic Acid ppm | Ethanol % v/v | Diacetyl ppm | Color | pH |
|---|---|---|---|---|---|---|
| Feed-100 proof | | 44 | 51 | 83 | slight green | 4.45 |
| 1% H$_2$O$_2$ (7%) + 0.01% NaOH (50%) | 462.7 | 195 | 51 | ND | clear | 6.8 |
| Distillate | 134.9 | ND | 101 | ND | clear | 9.45 |
| Still Bottoms | 321.2 | 237 | 26 | ND | clear | 5.08 |

Several batch distillations were completed to determine alternate treatments that remove the diacetyl but maintains the ethanol in a more desirable pHe. The test results are displayed in Table 4 for the mitigation treatment of 2% by volume of a 7% H$_2$O$_2$ solution followed by 0.2% by volume of a 1.0N NaOH solution. The distillate was clear in color, the HPLC results confirm there was no diacetyl and the pH is lower.

TABLE 4

H$_2$O$_2$ + NaOH Mitigation - 2.0% H$_2$O$_2$ (7% H$_2$O$_2$) +
0.2% NaOH (1.0N) in 200 Bell ethanol diuted to 100 proof

| Distillations Fraction # | Mass (g) | Acetic Acid ppm | Ethanol % v/v | Diacetyl ppm | Color | pH | pHe |
|---|---|---|---|---|---|---|---|
| Feed-100 proof | | 25 | 51 | 100 | slight green | 4.42 | |
| 2% H$_2$O$_2$ (7%) | | 68 | 50 | 59 | slight green | 4.23 | |
| 0.2% NaOH (1.0N) | 462.5 | 143 | 50 | ND | clear | 6.52 | |
| Distillate | 139.1 | ND | 99 | ND | clear | | 7.64 |
| Still Bottoms | 319.1 | 257 | 25 | BDL | clear | 4.88 | |
| Feed-100 proof | | 32 | 51 | 102 | slight green | 4.43 | |
| 2% H$_2$O$_2$ (7%) | | 131 | 50 | 35 | slight green | 4.23 | |
| 0.2% NaOH (1.0N) | 463.0 | 149 | 50 | ND | clear | 6.54 | |
| Distillate | 131.5 | ND | 99 | ND | clear | | 8.06 |
| Still Bottoms | 324.1 | 228 | 26 | BDL | clear | 5.02 | |
| Feed-100 proof | | 23 | 51 | 97 | slight green | 4.41 | |
| 2% H$_2$O$_2$ (7%) | | 88 | 50 | 54 | slight green | 4.26 | |
| 0.2% NaOH (1.0N) | 470.6 | 146 | 50 | ND | clear | 6.53 | |
| Distillate | 129.3 | ND | 101 | ND | clear | | 7.10 |
| Still Bottoms | 323.4 | 246 | 25 | ND | clear | 4.84 | |

Example 4

An example was performed at elevated temperature. A sample of cellulosic 100 proof ethanol was subjected to the mitigation treatments of 10% and 5% by volume of a 7% H$_2$O$_2$ solution, 0.1% by volume of a 50% w/w NaOH solution, 0.2% by volume of a 1N NaOH solution, and 2% by volume of a 7% H$_2$O$_2$ solution followed by 0.2% by volume of a 1N NaOH solution. The samples were placed into a 60° C. water bath immediately after being dosed with the treatment at time zero. Samples were removed from the heated water bath and placed into an ice bath at set time points, and then analyzed by HPLC. Samples that were treated with stronger doses of sodium hydroxide turned yellow-orange immediately after addition, and darkened to a pink color after time at the elevated temperature. When left at room temperature overnight, all samples had changed to the same pink color. Lower doses of sodium hydroxide resulted in less color, and the combination treatment of hydrogen peroxide and sodium hydroxide showed no color change.

Figure 5:
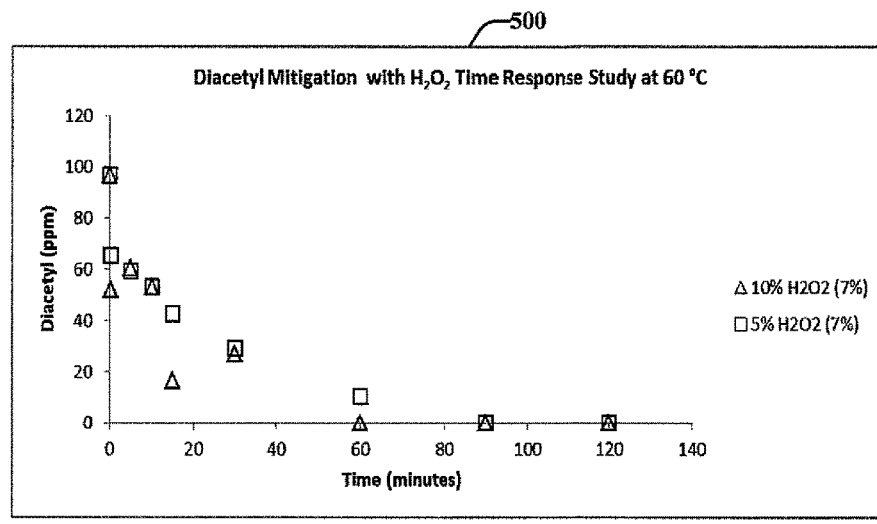
FIG. 5 shows a graph of diacetyl concentration over time in peroxide treated samples according to Example 4.
Figure 6:
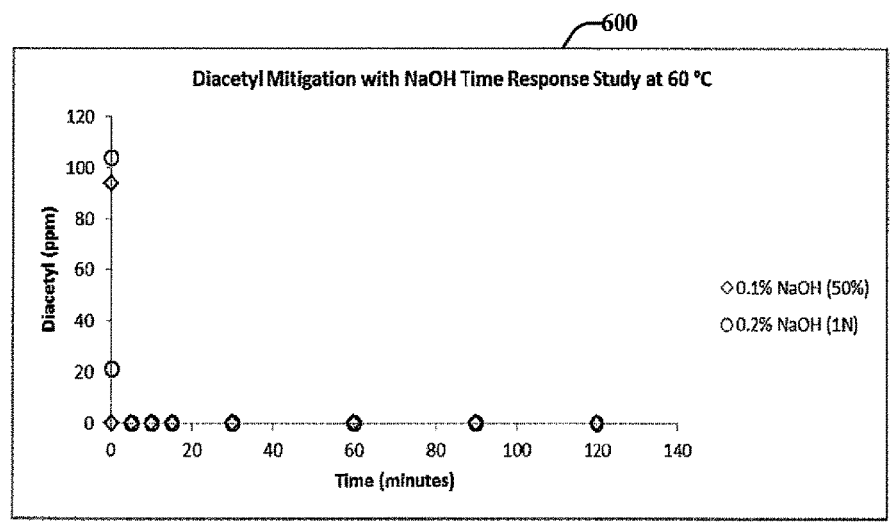
FIG. 6 shows a graph of diacetyl concentration over time in alkali treated samples according to Example 4.
Figure 7:
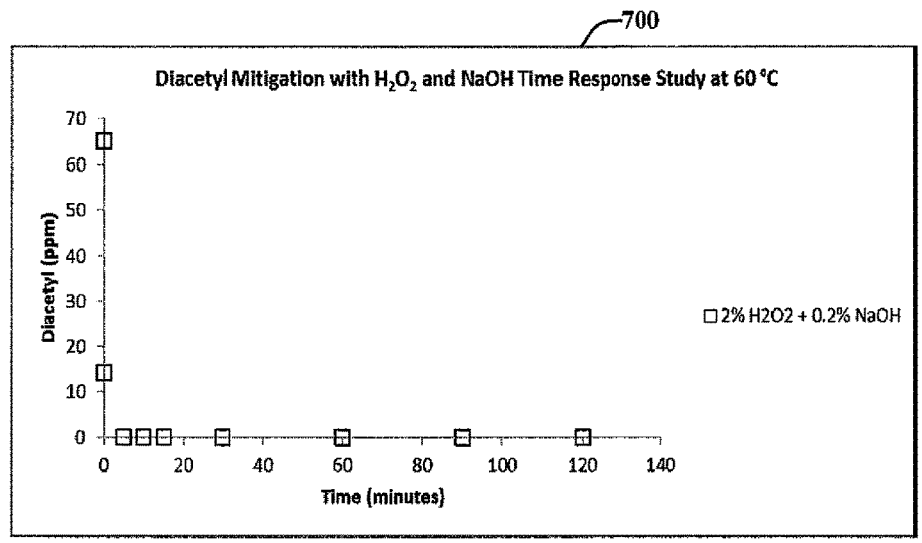
FIG. 7 shows a graph of diacetyl concentration over time in peroxide and alkali treated samples according to Example 4.

FIGS. 5-7 illustrate the results of this example study. In FIG. 5, the samples treated with H$_2$O$_2$ are illustrated as the diacetyl concentration over time (at 500). Diacetyl levels decrease over time and reaches very low levels at approximately 60 minutes. In FIG. 6, the samples treated with NaOH are illustrated as the diacetyl concentration over time (at 600). Here the diacetyl decreases almost instantaneously after caustic application. A similar response is seen in FIG. 7, where samples treated with NaOH and H$_2$O$_2$ are illustrated (at 700).

Example 5

Figure 8:
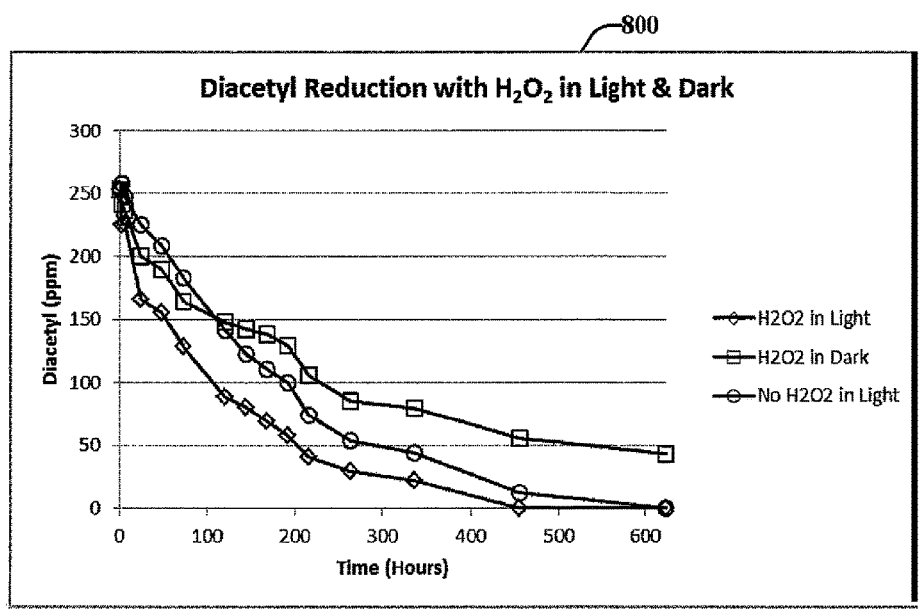
FIG. 8 shows a graph of diacetyl concentration over time in peroxide treated samples when exposed to light or darkness in accordance with Example 5.

A further example for mitigation treatments illustrates that that exposure to light also reduces diacetyl in cellulosic ethanol. Samples of 200 proof cellulosic ethanol were tested under three different conditions. The first was placed in a capped glass jar that was placed in the hood under light 24/7, the second was treated with 0.1% by volume of a 7% H$_2$O$_2$ solution (one dose at time zero only) and stored in the hood under light 24/7, and the third was treated with 0.1% by volume of a 7% H$_2$O$_2$ solution then placed in the dark. Aliquots of each sample were taken periodically and analyzed on the HPLC. FIG. 8 shows the trend for the diacetyl reduction in these three conditions. The samples treated with peroxide showed an initial reduction more pronounced than the sample not treated with peroxide, however light also affect the speed of diacetyl reduction. The sample stored in the dark showed the slowest reduction over time.

Example 6

Figure 9:
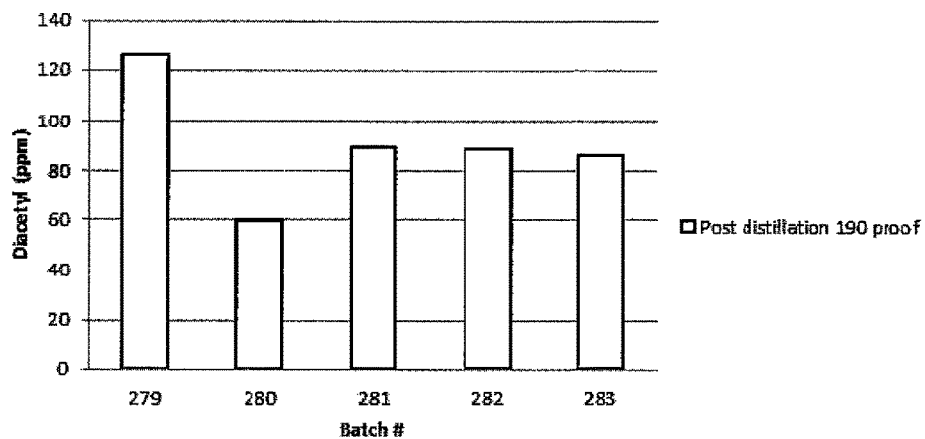
FIG. 9 shows a graph of diacetyl concentration over various fermentation batches according to Example 6.

The diacetyl mitigation process was also demonstrated in a larger pilot plant. FIG. 9 describes the diacetyl concentration in the 190 proof samples collected after distilling five fermentation batches. The concentration of diacetyl in the distilled 190 proof ranged from 60 ppm to 126 ppm and averaged 90 ppm. Among other final product specifications affected by the presence and composition of diacetyl, color is the most prominent. The visible color threshold in this example is shown to be around 20-30 ppm diacetyl.

Grab samples were collected for each of five fermentation batches through distillation, as well as two composite samples. The ethanol concentration of the five fermentation batches averaged 89.96% (≈180 proof), while composite samples at 24 hours and 48 hours averaged 83.57%. The difference in ethanol concentration is presumably from startup and shutdown procedures for distillation that allow more water to stay in vapor form. The pHe of the ethanol samples decreased as acetic acid concentration increased over time in storage as a result of diacetyl degradation. The acetic acid formed from diacetyl significantly increases the amount of NaOH required for mitigation.

Figure 10:
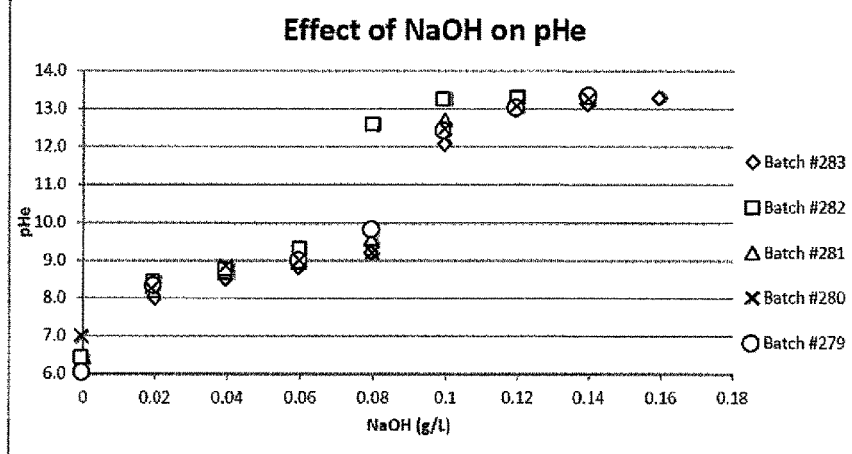
FIG. 10 shows a graph of pH of ethanol dependent upon alkali treated samples according to Example 6.
Figure 11:
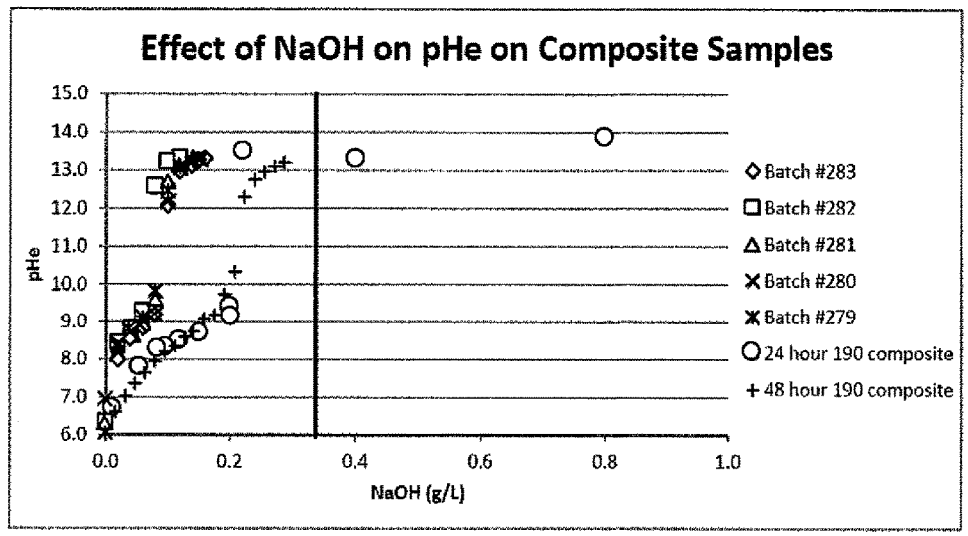
FIG. 11 shows a graph of pH of ethanol dependent upon alkali treated composite samples according to Example 6.

FIG. 10 describes the effect of NaOH on the pHe of the batch grab samples of 190 proof ethanol. FIG. 11 shows the NaOH and pHe relationship for the 24 and 48-hour composite samples, overlaid with the grab samples. From the data presented in FIG. 10, a significant increase in pHe was observed between 0.08 g/L and 0.12 g/L NaOH for individual grab samples. However, FIG. 11 shows the NaOH dose required to reach target pHe is increased to 0.22 g/L NaOH in the composite 190 proof samples due to the presence of acetic acid.

Figure 12:
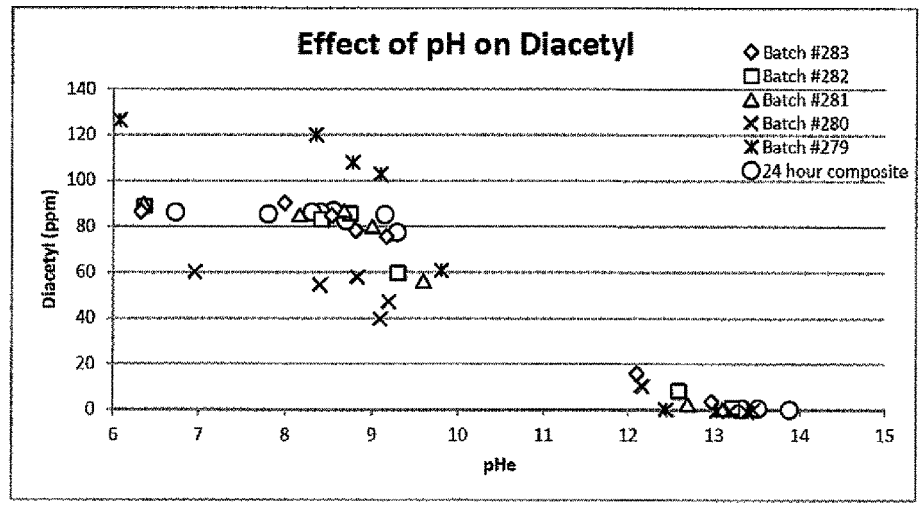
FIG. 12 shows a graph of diacetyl concentration dependent upon pH according to Example 6.

FIG. 12 details the effect of pHe on diacetyl concentration for the grab and 24-hour composite 190 proof samples. From this figure, a pHe greater than 12.5, in general, reduced diacetyl concentrations to less than 10 ppm, with complete diacetyl destruction occurring after the pHe reached 13.0 for all samples analyzed.

The 190 proof grab samples required between 0.10 and 0.14 g/L NaOH to achieve a diacetyl concentration below detectable limits. However, the 24 and 48-hour composite samples required 0.22 and 0.27 g/L NaOH, respectively, to reach 13.0 pHe for complete diacetyl mitigation. Using the 48-hour composite titration result from FIG. 11, including an additional 20% safety factor, the dosing requirement to reach 13.0 pHe for pilot scale mitigation was determined to be 0.35 g/L NaOH.

Figure 13:
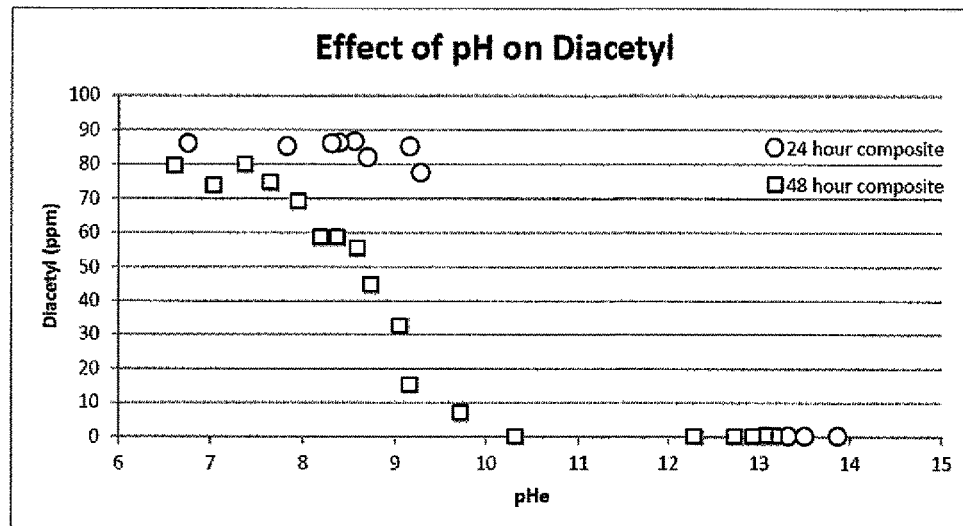
FIG. 13 shows a graph of diacetyl concentration dependent upon pH for composite samples according to Example 6.

FIG. 13 compares the composite 190 proof ethanol samples. The 24-hour composite sample was processed on the HPLC immediately following NaOH titration. The resulting pHe vs. diacetyl curve closely matches the grab samples in that there was a definitive break in pHe value before a reduction in diacetyl concentration was observed. The 48-hour pHe vs. diacetyl curve was affected by increased reaction time between titration with NaOH and HPLC analysis.

Figure 14:
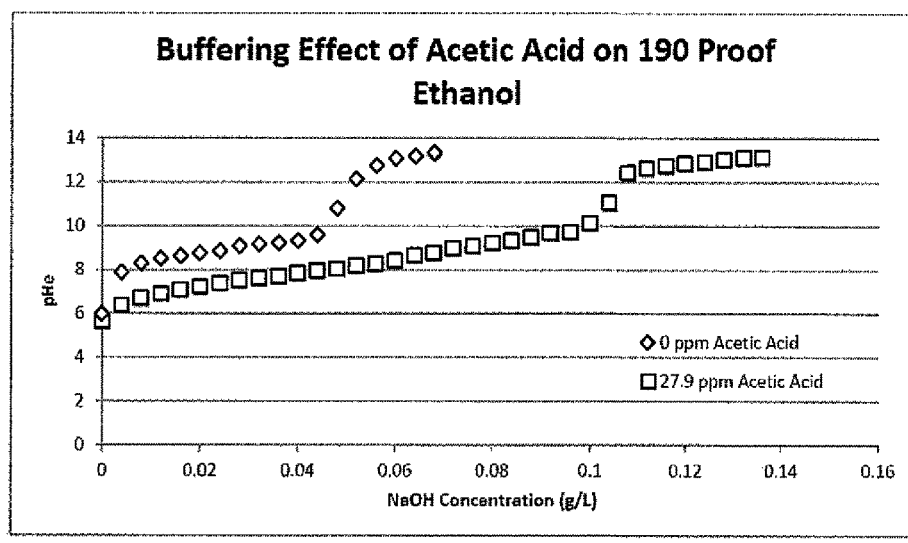
FIG. 14 shows a graph of pH of ethanol dependent upon alkali treatment for acetic acid buffered samples according to Example 6.

The principle difference between the composite and grab samples was the presence of acetic acid. No acetic acid was detected in the grab samples, while the 24 and 48-hour composite samples contained 27 ppm and 52 ppm acetic acid, respectively. The samples of 190 proof starch ethanol containing 0 and 27.9 ppm acetic acid were titrated and the results are presented in FIG. 14 which shows the dosage of NaOH required to adjust the samples to a pHe of 13.0. The sample containing no acetic acid required only 0.06 g/L NaOH to reach the desired pHe of 13.0. However, the sample containing 30 ppm acetic acid significantly increased the buffering capacity of the ethanol, requiring nearly 0.13 g/L NaOH.

This acetic acid buffering effect directly influences the amount of NaOH required for dosing. If the acetic acid concentration present in the 190 proof cellulosic ethanol can be held to a minimum, the NaOH dose required for ethanol is reduced from 0.35 g/L to 0.14 g/L NaOH (including the 20% safety factor).

Lastly, in order to more accurately reflect commercial scale remedial systems, an example is provided where a forced circulation evaporator was used to vaporize pH adjusted cellulosic 190 proof ethanol at atmospheric pressure. A steady flow of 190 proof ethanol was supplied at 0.9-0.75 gpm to the separator of the evaporator. A peristaltic pump was used to supply 1N NaOH to the vaporizer feed line at a targeted 0.35 g/L NaOH. Steam pressure was controlled to produce a steady distillate flow. A purge, or recycle, stream was operated to maintain a steady level in the separator. The distillate stream and the concentrate purge stream were collected separately for analysis.

Figure 15:
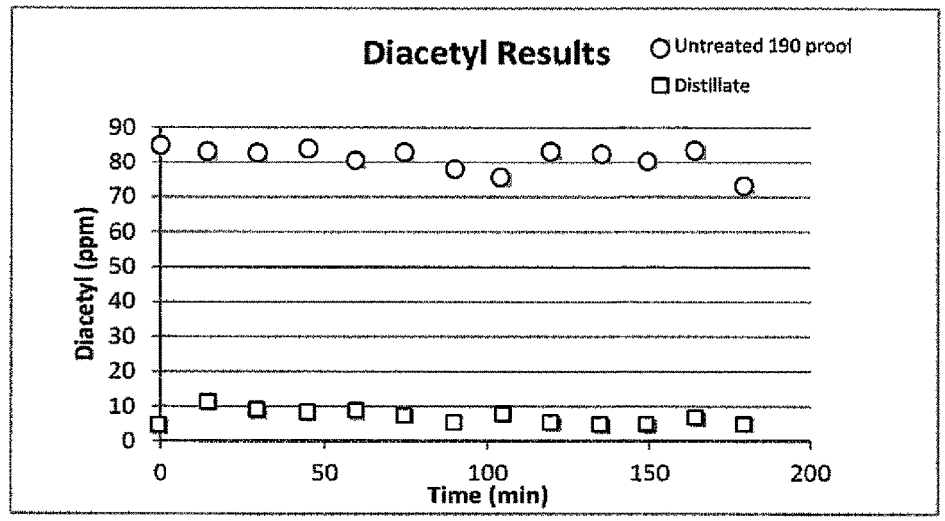
FIG. 15 shows a graph of diacetyl concentration for untreated samples and treated distillate according to Example 6.

FIG. 15 shows the diacetyl concentration in the untreated 190 proof was reduced from 80 ppm to <10 ppm with an average value of 6.4 ppm. HPLC analysis was also performed on both the feed and concentrate streams.

Figure 16:
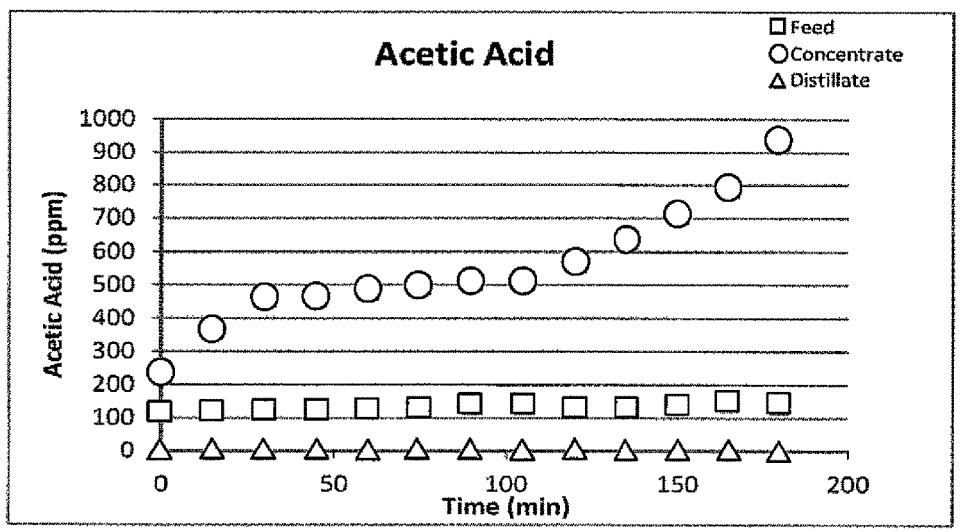
FIG. 16 shows a graph of acetic acid concentration of the feed, concentrate and distillate over time according to Example 6.

Acetic acid present in the composite 190 proof ethanol sample accumulated in the vaporizer and had not reached equilibrium with purge volume by the end of the experiment. FIG. 16 shows the acetic acid present in the feed and its accumulation in the vaporizer.

What is claimed is:

1. A method of reducing the concentration of diacetyl that is present in a distillate comprising:
    providing a pretreated cellulosic material;
    subjecting the pretreated cellulosic material to a fermentation process to form a fermentation product comprising:
        an alcohol; and
        diacetyl;
    distilling the fermentation product to form a distillate comprising the alcohol and the diacetyl; and
    contacting the distillate with at least one treatment compound so that the at least one treatment compound reacts with the diacetyl to form a reaction product thereby reducing the concentration of the diacetyl and forming a treated distillate, wherein the at least one treatment compound is chosen from an oxidizing agent and mixtures of the oxidizing agent and an alkali.

2. The method of claim 1, further comprising subjecting the treated distillate to a vaporization process to vaporize at least a portion of the treated distillate to form a liquid fraction and a vapor fraction, wherein the vapor fraction comprises at least a portion of the alcohol and the concentration of the alcohol in the vapor fraction is higher as compared to the concentration of the alcohol in the treated distillate.

3. The method of claim 2, wherein the liquid fraction from the vaporization process comprises at least a portion of the reaction product and the concentration of the reaction product in the liquid fraction is higher as compared to the concentration of the reaction product in the treated distillate.

4. The method of claim 3, wherein the vapor fraction from the vaporization process comprises diacetyl in an amount of 50 parts per million or less.

5. The method of claim 4, wherein the vapor fraction from the vaporization process comprises at least 100 proof ethanol.

6. The method of claim 1, wherein the oxidizing agent comprises hydrogen peroxide.

7. The method of claim 1, wherein the alkali compound comprises sodium hydroxide.

8. The method of claim 7, wherein the distillate is contacted with an amount of sodium hydroxide so that the pH of the distillate is at least 10.

9. The method of claim 8, wherein the distillate is contacted with an amount of sodium hydroxide so that the pH of the distillate is at least 12.

10. The method of claim 1, wherein the distillate comprises ethanol, wherein the diacetyl is present in the distillate at a concentration of at least 50 parts per million, and the distillate is contacted with an amount of sodium hydroxide so that the concentration of diacetyl is reduced to 20 parts per million or less in a time period of twenty minutes or less.

11. A method of reducing the concentration of diacetyl that is present in a distillate comprising:
    providing a pretreated cellulosic material;

subjecting the pretreated cellulosic material to a fermentation process to form a fermentation product comprising:
an alcohol; and
diacetyl;
distilling the fermentation product to form a distillate comprising the alcohol and the diacetyl; and
contacting the distillate with at least one treatment compound so that the at least one treatment compound reacts with the diacetyl to form a reaction product thereby reducing the concentration of the diacetyl and forming a treated distillate, wherein the at least one treatment compound is chosen from an oxidizing agent, an alkali compound, and mixtures thereof; and
exposing the distillate to ultraviolet light to reduce the concentration of the diacetyl, wherein the exposing the distillate to ultraviolet light can occur before, during, or after contacting the distillate with at least one treatment compound.

* * * * *

UNITED STATES PATENT AND TRADEMARK OFFICE
CERTIFICATE OF CORRECTION

PATENT NO. : 10,213,704 B2  
APPLICATION NO. : 14/993285  
DATED : February 26, 2019  
INVENTOR(S) : David Charles Carlson et al.

It is certified that error appears in the above-identified patent and that said Letters Patent is hereby corrected as shown below:

On the Title Page

Item (60) "61/600,043" should be -61,660,043-

Signed and Sealed this  
Ninth Day of July, 2019

Andrei Iancu  
*Director of the United States Patent and Trademark Office*